US00PP34707P2

(12) United States Plant Patent
Hansen

(10) Patent No.: US PP34,707 P2
(45) Date of Patent: Nov. 1, 2022

(54) ***BAPTISIA* PLANT NAMED 'HONEY ROASTED'**

(50) Latin Name: ***Baptisia* hybrid**
Varietal Denomination: Honey Roasted

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,084

(22) Filed: Feb. 1, 2022

(51) Int. Cl.
*A01H 5/02* (2018.01)
*A01H 6/54* (2018.01)

(52) U.S. Cl.
USPC ..... Plt./263.1
CPC ..... *A01H 6/54* (2018.05)

(58) Field of Classification Search
USPC ..... Plt./263.1
CPC ..... A01H 5/02
See application file for complete search history.

*Primary Examiner* — Kent L Bell

(57) ABSTRACT

A new and distinct cultivar of hardy herbaceous False Indigo plant named 'Honey Roasted' characterized by flowers that open up dark mahogany with a complementary bright yellow keel beginning in late May and continuing for two to three weeks. The new plant has a narrow, medium-height, upright, mounded shaped, multi-stemmed, winter-hardy habit with glaucous dark-green tri-foliate foliage and is suitable for landscaping as a specimen or en masse.

2 Drawing Sheets

Botanical classification: *Baptisia* hybrid.
Cultivar designation: 'Honey Roasted'.

STATEMENT REGARDING PRIOR DISCLOSURES UNDER 37 CFR 1.77(B)(6)

*Baptisia* 'Honey Roasted' was promoted in a non-enabling description and photographs on a website operated by Walters Gardens, Inc. on Feb. 1, 2021, followed by the "Walters Gardens 21-22 Catalog" initially distributed by Walters Gardens, Inc. on May 21, 2021. The first enabling disclosure of *Baptisia* 'Honey Roasted', in the form of a sale, was made by Walters Gardens, Inc. on May 3, 2021 to K Drive Greenhouse, Co. Information and plants for this sale and all sales thereafter were obtained from the inventor. No plants of *Baptisia* 'Honey Roasted' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Honey Roasted' and will be referred to hereafter by its cultivar name, 'Honey Roasted', and the new plant. The new plant represents a new false indigo, a hardy herbaceous perennial grown for landscape and cut flower use.

'Honey Roasted' arose from an ongoing breeding program of the inventor at a nursery in Waseca, Minn. with continued evaluation at a wholesale perennial nursery in Zeeland, Mich. with the specific intention of improving garden worthiness of perennial false indigo plants with a wider variety of flower colors and improved garden habit.

*Baptisia* 'Honey Roasted' was a single seedling selection from a cross between a proprietary unreleased hybrid selection named by the breeder code "Candy" (not patented) as the female or seed parent times 'Blueberry Sundae' (U.S. Plant Pat. No. 23,891) as the male or pollen parent. Seeds were collected from the individual selected female plant in fall of 2009 at the isolation block in Waseca, Minn., USA by the inventor. The seeds were sown by the inventor at a wholesale perennial nursery in Zeeland, Mich. in the fall of 2009 and the initial selection made in the spring of 2011 at the same nursery in Zeeland and given the breeder code H9-9-01.

'Honey Roasted' was initially asexually propagated by stem cuttings at a wholesale perennial nursery in Zeeland, Mich. in 2015. The resultant plants have demonstrated that the new plant has remained stable and true to type in successive generations of asexual propagation.

The nearest comparison plants known to the inventor are: 'Cherries Jubilee' U.S. Plant Pat. No. 23,907, and 'Brownie Points' U.S. Plant Pat. No. 26,624.

'Cherries Jubilee' has a shorter inflorescence and broader habit and the flowers are maroon with yellow and age to gold and the flowers would appear more starting inside the foliage. 'Brownie Points' is larger in size but has caramel-brown flowers with yellow keels.

The female parent is smaller in habit and has butterscotch-colored flowers. The male parent has similar habit, but the flowers are blue.

The new plant differs from all *Baptisia* known to the inventor in the following combined traits:

1. Numerous flowers occur on long spikes;
2. Flowers open dark mahogany with a complementary bright yellow keel;
3. Flowering begins about late-May in Michigan and continues for two to three weeks;
4. Narrow, medium-height, upright, mounded shaped, multi-stemmed, winter-hardy habit;
5. Glaucous, dark-green, tri-foliate foliage.

BRIEF DESCRIPTION OF THE DRAWINGS

The photographs of 'Honey Roasted' demonstrate the unique traits of the new plant and the overall appearance.

The colors are as accurate as reasonably possible with color reproductions. Variation in ambient light spectrum, source and direction may cause the appearance of minor variation in color. The accompanying photograph is of an eight-year-old plant growing in an open full-sun trial garden in Zeeland, Mich.

DETAILED BOTANICAL DESCRIPTION OF THE PLANT

Figure 1:
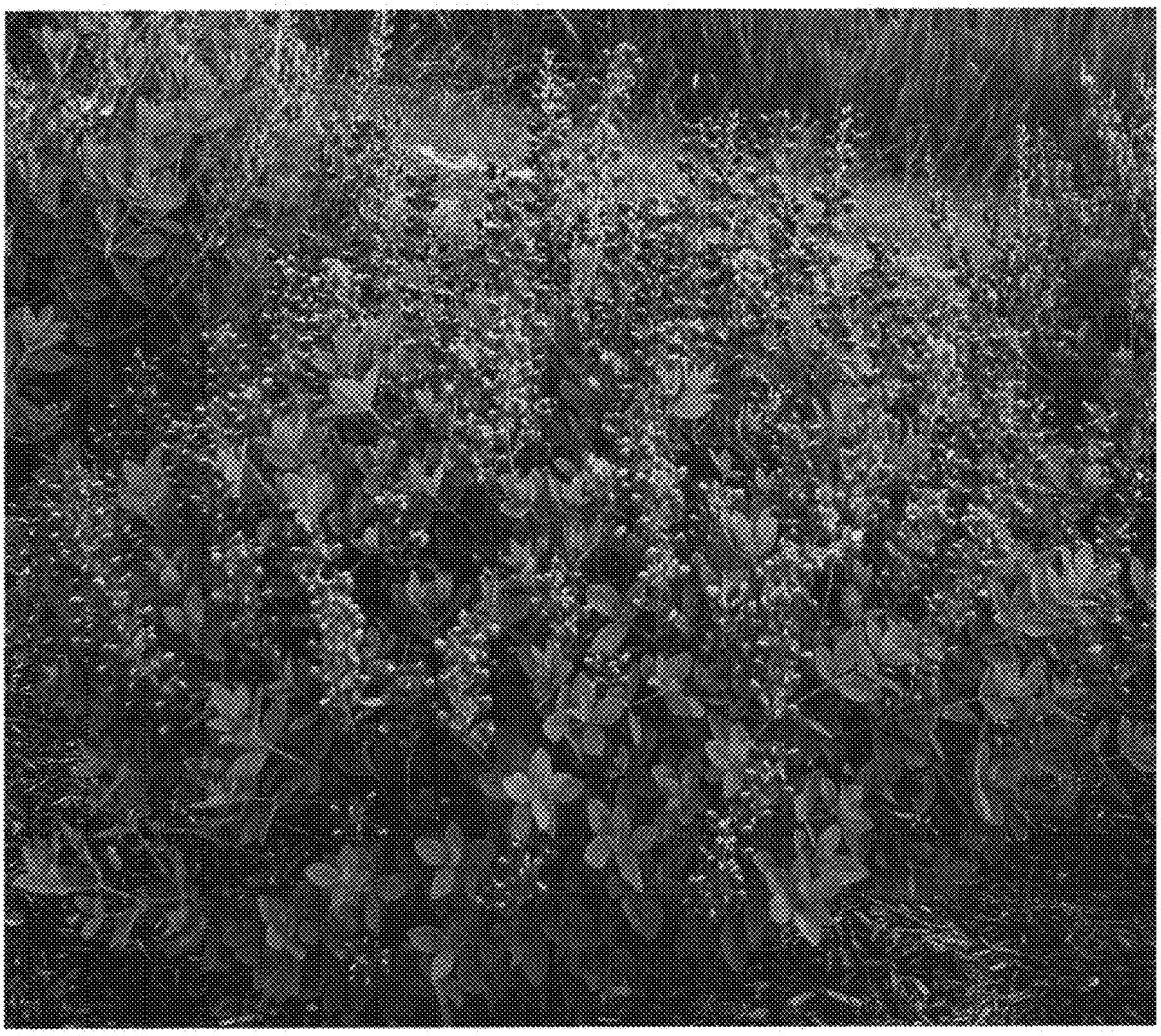
FIG. 1 shows the habit of a plant in full flower.
Figure 2:
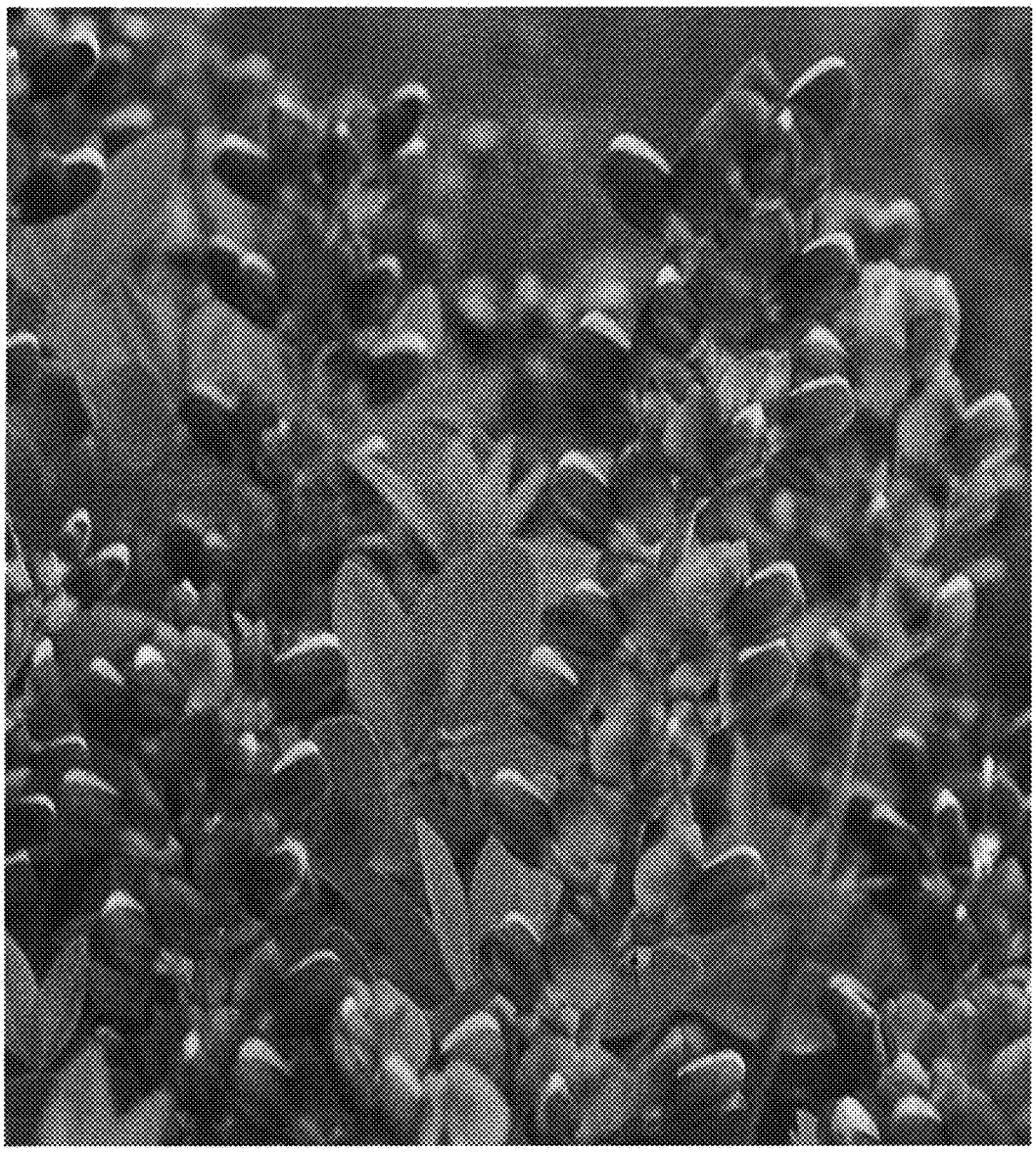
FIG. 2 shows a close-up of the inflorescence.

The following is a detailed description of twelve-year-old plant of 'Honey Roasted' as grown outdoors in a trial block and two-year-old plants grown in a partially shaded greenhouse at a wholesale perennial nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, well-branched, many-stemmed, vase-shaped growth habit with long inflorescences held above the foliage;

Plant size: Stems and crown about 28 cm across at soil level, at flowering about 105 cm tall from soil to top of flowers and 122 cm wide about 50 cm above soil; at maturity plant foliage height about 105 cm tall and about 122 cm wide;

Roots: Fibrous, well-branched, long, deeply rooted;

Root color: Nearest RHS 161D;

Propagation method: Stem cuttings, rooting in about three weeks;

Growth rate: Moderate to average;

Stems: Rigid and upright; highly glaucous; glabrous; cylindrical with shallow longitudinal furrows; lower two to three nodes without leaves or branches; normally two to three branches per plant below flowers; about 55 stems per clump;

Stem size: Main stem to about 9 mm diameter at base and 105 cm tall, average about 98 cm long and about 9 mm diameter; to about 50 cm long from soil to below initial flowers;

Stem branches: Primary branches at 45 to 60-degree angle above horizontal, up to 30 cm long and 5 mm diameter, average for primary branches about 25 cm long and 4 mm diameter, smaller distally; and three to six alternate secondary branches per stem of about 17 cm long and 3 mm diameter, averaging about 13 cm long and 3 mm diameter;

Stem color: Between RHS N138D and RHS 194D;

Stem scales: At stem nodes; lanceolate; emarginate to retuse apex with sharply pointed sides; truncate clasping base; margin entire; dehiscing to leave behind thin scar on stem; about 18 mm wide at base and 21 mm wide in center; about 18 mm long and 2 mm wide in center of apex;

Stem scale color: Variable, nearest RHS N138D, between RHS 146B and RHS 147B, and RHS N186A before dehiscing;

Internodes: Up to 9 cm apart between lowest branches, average about 6 cm;

Internode color: Variable, nearest RHS 139D, RHS 148D and nearest RHS N186A;

Foliage: Alternate; ternate to palmately compound with three leaflets; outer two leaflets independent, at nearly 90-degree angle to middle leaflet; up to 8 cm long and 12.5 cm wide;

Leaflet: Three; oblanceolate; apex acute, base cuneate; margins entire; petiolate; adaxial surfaces matte, glabrous and slightly glaucous, abaxial slightly glaucous and glabrescent becoming matte; middle lobe to about 7.5 cm long and 3.5 cm wide, side lobes about 6.8 cm long and 2.9 cm wide;

Leaflet color: Newly expanding adaxial between RHS 137A and RHS NN137A, abaxial nearest RHS 137A; mature adaxial nearest RHS 138A, abaxial between RHS 138A and RHS 138B;

Venation: Pinnate, glabrous, thin, not conspicuous;

Vein color: Newly expanding foliage adaxial midrib and primary veins between RHS 145C and RHS 146D, abaxial nearest RHS 147C; mature adaxial midrib and secondary veins nearest RHS NN137B, abaxial midrib lighter than RHS 145D and secondary veins nearest RHS 137C;

Petioles: Glabrescent; slightly glaucous; concavo-convex; to about 10 mm long and 2 mm wide at base, average 5 cm long and 1.5 mm wide;

Petiole color: Adaxial center nearest 145A and margin nearest RHS 138A, abaxial nearest RHS 147C;

Stipules: Narrowly lanceolate, narrowly acute apex with base truncate; to about 25 mm long and 7 mm wide, average 16 mm long and 5 mm wide with largest stipules below primary branches and decreasing distally and on secondary branches;

Stipule color: Nearest RHS 138A both surfaces;

Peduncle: Cylindrical with vertical shallow ridges and furrows; glaucous; glabrous; from first flower to apex about 26 cm long; diameter at the base of first flower about 3.5 mm and about 2 mm diameter at the apex;

Peduncle color: Between RHS N187A and RHS N186A in the flowering portions;

Pedicel: Cylindrical, glabrous, glaucous; about 5 mm long and 1 mm diameter;

Pedicel color: Nearest RHS 146B;

Calyx: Campanulate; four-lobed; to about 8 mm long, 8 mm tall and 9 mm across at apex;

Sepals: Four; one larger dorsal, one ventral and two lower lateral; acute apices; fused into tube in proximal 6 mm; margin entire; glabrous adaxial and abaxial; dorsal sepal to about 9 mm long and 5 mm wide at fusion; other three sepals to about 9 mm long and 4 mm across at fusion;

Sepal color: Adaxial nearest RHS 145C; abaxial nearest RHS 150C with light tinting of nearest RHS 146D distally;

Buds one day prior to anthesis: Oblong elliptic, flatted vertically; to about 25 mm long and 12 mm tall and 9 mm wide, slightly smaller in distal flowers;

Bud color one day prior to anthesis: Exposed keel petal blend nearest RHS 5A, enfolded banner petal between RHS N186B and RHS 187A in dorsal center, sides nearest RHS 5A with minor veins and moderate blushing nearest RHS 187A, exposed alae petals ventrally nearest RHS 5A and dorsally transitioning to between RHS 166A and RHS 176A;

Flower: Zygomorphic, papilionaceous, non-secund, held at about a 45-degree angle above horizontal; to about 48 flowers per main raceme and about 17 per secondary branch; seasonally effective for at least 2 weeks beginning in late May in Zeeland, Mich.;

Lasting: Individual flowers remain effective as cut flowers and on raceme for about four days; individually to about 25 mm long, 16 mm tall and 18 mm wide at largest portions; consisting of an upper banner, a lower keel made up of two lobes folded around gynoecium and androecium; and two lateral wings or alae laterally appressed against keel;

Flower fragrance: None detected;

Petals: Five; with a lower fused keel, an upper banner, and two lateral wings or alae; keel comprised of two sections that are folded around stamens and pistil;

*Banner petal*.—Conduplicate, reflexed upward and backward and pinched in the middle; apex retuse, base claw-like, margin entire; to about 20 mm long, 16 mm across natural width, 20 mm wide flattened spread and 12 mm tall; with rounded emarginate apex notched about 2 mm deep; basal portion attenuate claw-type, 5 mm long and 2 mm wide at base.

*Banner color*.—Upon first opening — adaxial distal margin nearest RHS 5A, center between RHS 166A and RHS 176A with faint veins and blushing between center and margin and claw nearest RHS 2B; abaxial center nearest RHS N186B, distally lightly blushed and veined with nearest RHS 177A with claw nearest RHS 145C; mature adaxial and abaxial claw nearest RHS 145D and blade portion between RHS 177D and RHS 166D.

*Keel*.—Comprised of two main lobes that are folded around stamens and pistil; fused in the distal one-third with the apex emarginate or retuse and the bases separate and claw-like; margin entire; top edge about one-third of the way from base has 2 mm smaller lobe pointing toward base; about 21 mm long and 10 mm tall and 2 mm wide; blade portion to about 17 mm long and 10 mm tall, with claw to about 7 mm long and base narrowed to 2 mm wide at base.

*Keel color*.—Upon first opening — adaxial base nearest RHS 145C, distal portion nearest RHS 5A and proximal portion nearest RHS 4C; abaxial keel distal portion nearest RHS 5A proximal portion RHS 4C, base nearest RHS 145C; mature between RHS 11A and RHS 11B and base nearest RHS 145D.

*Alae*.—Two; papilionaceous corolla appendage with rounded apex and claw-like base; with 2 mm long by 2 mm wide lobe pointing toward base and about one-third of the way from base; about 21 mm long and 10 mm tall with the claw to 3 mm wide at base of blade and 2 mm wide at base and 7 mm long; blade about 17.mm long and 10 mm wide.

*Alae color*.—Upon first opening — adaxial claw base between RHS 150C and RHS 150D, dorsal main blade portion and lobe nearest RHS 4A and ventral main blade moderately blushed with nearest RHS 177A; abaxial claw base nearest RHS 150D, lobe and main blade dorsal portion nearest RHS 5A and main blade ventral portion between RHS 177A and RHS 167A; mature between RHS 11A and RHS 11B, with claw nearest RHS 145D.

Receptacle: Disk-shaped, about 3 mm diameter and 2.5 mm depth; color between RHS 138A and RHS 137B;

Gynoecium: One, with superior ovary and stipe; to about 20 mm long;

*Style*.—Cylindrical; glabrous; slightly glaucous; tapered and curved upwardly distally, about 8 mm long and about 0.7 mm diameter above ovary; color nearest RHS 145B.

*Stigma*.—About 0.2 mm diameter; color nearest RHS NN155A.

*Ovary*.—Superior above hypanthium, suspended by stipe; about 7 mm long and about 1.5 mm in diameter; color between RHS 150D and RHS N144D.

*Stipe*.—Cylindrical; glabrous; slightly glaucous; about 5 mm long and 0.7 mm diameter; color nearest RHS 145B.

Androecium:

*Stamens*.—Ten.

*Filament*.—Glabrous; slightly lustrous; not united 20 mm in length and about 0.5 mm in diameter; slightly curved upwardly distally; color nearest RHS 145D.

*Anther*.—Dorsifixed, oblong; about 2 mm long and 1.2 mm wide; color nearest RHS 17A.

*Pollen*.—Spherical; abundant; color nearest RHS 17A.

Fruit: Bivalve inflated ellipsoidal pod; glabrous; about 30 mm long, 18 mm across and 13 mm thick; with thin, linear, arcuate, terminal beak about 3 mm long and about 1 mm thick; rounded base;

Fruit color: At maturity between 200A and RHS 202A;

Seeds: About 8 per pod (open pollinated); reniform; glabrous; about 4.0 mm long, 3.0 mm across and 2.0 mm thick; color nearest RHS N199C;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed;

It is claimed:

1. A new and distinct cultivar of *Baptisia* plant named 'Honey Roasted' as herein described and illustrated.

* * * * *